US00PP10336P

United States Patent [19]

Sorensen

[11] Patent Number: Plant 10,336

[45] Date of Patent: Apr. 21, 1998

[54] OSTEOSPERMUM PLANT NAMED 'CAPE DAISY ZIMBA'

[75] Inventor: Carl Aksel Kragh Sorensen, Åbyhoj, Denmark

[73] Assignee: Paul Ecke Ranch, Encinitas, Calif.

[21] Appl. No.: 695,341

[22] Filed: Aug. 9, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV-ROM Plant Variety Database 'Cape Daisy Zimba', PBR OTS0006+PBR 128 00005, 1994.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Cape Daisy Zimba', particularly characterized by its upright growth habit with excellent pure white flower color, early season flowering and medium green foliage, and suitability to 6 inch pots, nursery containers and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Cape Daisy Zimba', and was developed by the inventor Carl Aksel Kragh Sorensen in Aarhus, Denmark, in 1991, by crossing two seedling parents from my breeding program. Both seedlings are proprietary to the breeding program.

Asexual reproduction by terminal (stem tip) cuttings taken by me or under my supervision at Peterminde greenhouse in Aarhus, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. The only pure white ray flower color with yellow centers.

2. An upright compact growth habit.

3. Early flower response.

4. Well suited for 6" pots, nursery containers, and hanging baskets.

'Cape Daisy Zimba' is similar to the unpatented cultivar 'Sunny Boy'. The growth habit of 'Cape Daisy Zimba' is different in that the disk flowers are yellow, not blue, and leaves are darker green.

Chart A compares 'Cape Daisy Zimba' to 'Cape daisy Nairobi' which is the closest plant to the knowledge of the inventor. 'Cape Daisy Zimba' is a seed parent to 'Cape Daisy Nairobi', a plant described and illustrated in co-pending U.S. Plant patent application Ser. No. 08/698,341. The plant characteristics described in Chart A are based on three plants in one hanging basket.

CHART A

| Characteristic | 'Cape Daisy Zimba' | 'Cape Daisy Nairobi' |
|---|---|---|
| Plant Height (above the pot) | 32 cm | 28 cm |
| Plant Width | 66 cm | 50 cm |
| Flower Head Diameter | 7.5 cm | 7.7 cm |

-continued

CHART A

| Characteristic | 'Cape Daisy Zimba' | 'Cape Daisy Nairobi' |
|---|---|---|
| Inflorescence Color | White with yellow center | White with blue center |

DESCRIPTION OF PHOTOGRAPH

The accompanying colored photograph is a side perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinias, Calif. Three rooted cuttings were transplanted into 26 cm (10 inch) hanging baskets on Dec. 11, 1995. Plants were pinched on Jan. 2, 1996, and received plant growth regulator on January 16 and 31. The values, measurements and observations noted below were taken from plants in bloom on Feb. 29, 1996.

On Apr. 8, 1996, I observed a plant in a 26 cm hanging basket 32 cm tall. This basket had three branched plants with an overall height of 45 cm and an overall width of 66 cm. Each plant had 5 strong branches, originating from within 1.5 cm of the soil line, for a total of 15 branches. Each branch was approximately 33 cm long terminating in a flower. At observation, there were 36 flowers open and 81 flower buds in various stages of development. Three secondary shoots subtend the terminal flower from the top 3 nodes on the primary shoot. These secondary shoots also terminated in a flower.

Color references are made to The Royal Horticultural Society Colour Chart (R.H.S.), except where general terms of ordinary dictionary significance are used.

THE PLANT

Origin: Seedling from cross pollination.

Parentage: Cross between two proprietary Cape Daisy seedling parents.

Classification:

*Botanical.—Osteopermum ecklonis.*

*Common name.*—Osteospermum.

*Cultivar name.*—'Cape Daisy Zimba'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth retardant application.*—Standard growth retardant application for 'Cape Daisy Zimba' includes 1–2 applications of Daminozide/Butanedioic acid mono (2.2 dimethylhydrazide) at a rate of 2,500 ppm. Applications are made as foliar sprays. Growth retarding chemicals generally reduce plant height by ⅓.

Plant description:

A. *Form.*—Symmetrical, low-growing perennial shrub, with good branching characteristics after pinching, giving the plant a full appearance.

B. *Habit of growth.*—Upright habit, producing approximately 13–15 leaves per stem and terminating in flowers. After the initial flower is formed, typically three subordinate axillary shoots develop from the uppermost leaves producing additional flowering shoots. This process is continuous so long as night temperatures remain below 16° C.

C. *Foliage description.*— 1. Leaf shape: Obovate with acute tip and attenuate leaf base. 2. Leaf blade size: Mature leaves 7–10 cm long and 2–3 cm wide. 3. Petiole length: Approximately 3 cm in length. 4. Leaf Margin: Slightly sinuate with 3–5 pointed lobes on either side of the leaf blade. 5. Leaf texture: Slighty undulant and twisted at the tip. (i) Upper surface: Slightly pubescent with short, white trichomes evenly distributed throughout the leaf surface. (ii) Under surface: Glabrous. 6. Leaf color: Green. (i) Upper surface: Dark green; Near R.H.S. 147A. (ii) Under surface: Green; lighter than R.H.S. 147A. 7. Ventation: Palmately branched with a predominate light green mid-rib on the upper surface. One prominent mid-vein is slightly raised on the lower surface. Two less prominent veins are observed on lower and upper surfaces. 8. Foliage Fragrance: Characteristics Osteospermum plant fragrance, particularly notable when foliage is wet.

Flower description: Daisy type composite flower with disk and ray florets that close at night and open in the morning. The ligulate petal of the ray floret subtends the pistil. The disk florets contain male flower parts. Florets on the flower head are imperfect with pistillate ray florets and staminate disk florets.

A. *Flowering habits.*—Flowering is determinate with one primary flower at the end of a long, (16–18 cm) pedicel on open flowers. Each pedicel had approximately 4–6 leaflets on the proximal end of the pedicel. A secondary flower arises from the base of the primary pedicle.

B. *Natural flowering season.*—Flowering occurs primarily February through October in the northern hemisphere. Initiation occurs after a cool temperature vernalization (10°–17° C.). Floriferousness may wane during hot summer days in temperate climates. Rooted cuttings are pinched two weeks after potting, then cultivated at 10°–12° C. for four weeks, then maintained at 18° C. for seven weeks for a total of 13 weeks to flower.

C. *Flower buds.*—Flower buds develop successively on secondary branches, reaching a size of 2 cm long and 1 cm wide prior to opening.

D. *Flowers borne.*—Singularly 9–10 cm above the plant canopy.

E. *Quantity of flowers.*—Secondary flowers occur progressively around the primary flower so that tight buds to mature flowers are visible at the same time.

F. *Flower head.*—1. Number of florets: 20–24 ray florets and numerous disk florets, making up a flower disk approximately 1.2 cm in diameter. 2. Shape: Narrow linear florets with obtuse to acute tips and acute bases. Ray florets approximately 3.5 cm long and 0.9 cm wide. 3. Color: Ray florets are pure white: disk florets are yellow. (i) Upper surface of ray florets: Pure white, whiter than R.H.S. 155B. (ii) Under surface of ray florets: White with a yellow blush. Mostly white with some yellow stripes near R.H.S. 11C intensifying in color at the tip of each floret. (iii) Disk florets: Yellowish-white; near 158D. 4. Surface: (i) Upper surface of ray florets: Glabrous. (ii) Under surface of ray florets: Glabrous but pubescent near the base. 5. Inflorescence size: Up to 7.5 cm in diameter. 6. Flower fragrance: None.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2–3 mm long and white. 6. Ovary: Inferior to petals and green in color.

H. *Resistance.*—1. Frost: Withstands light frost. 2. Root, stem, foliage and flower diseases: High resistance.

What is claimed is:

1. A new and distinct cultivar of Osteospermum plant named 'Cape Daisy Zimba', as illustrated and described.

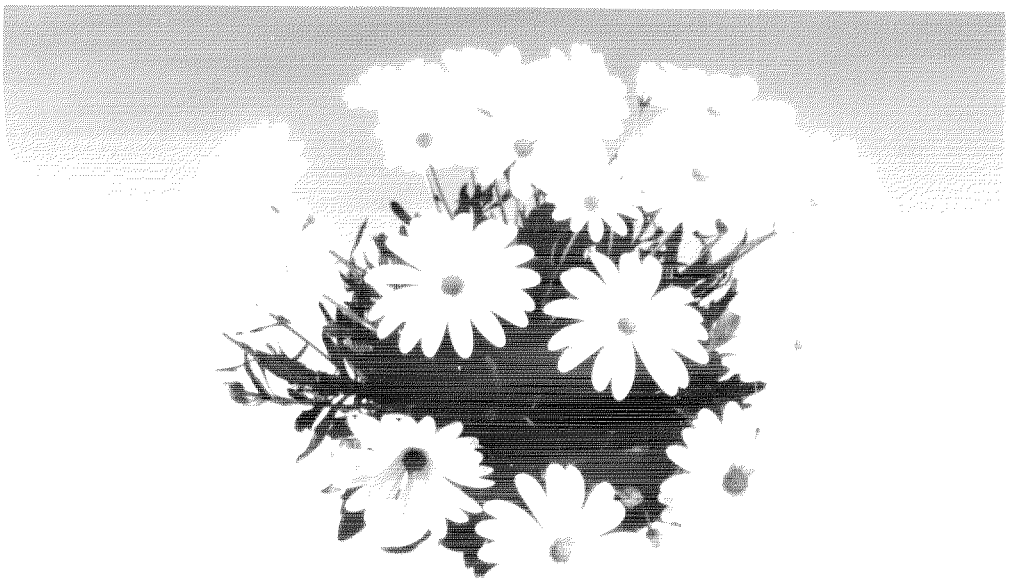

* * * * *